United States Patent
Tee, Jr. et al.

(10) Patent No.: US 10,940,059 B2
(45) Date of Patent: Mar. 9, 2021

(54) ARTICLE WITH ZEOLITES

(71) Applicant: The Procter & Gamble Company, Cincinnati, OH (US)

(72) Inventors: Johannson Jimmy Tee, Jr., Mason, OH (US); Kristin Hofmann Miller, Springboro, OH (US); William Winfield Cheeseman, Springboro, OH (US); Peter Dziezok, Hochheim (DE); Holger Beruda, Schwalbach am Taunus (DE); Marc Jennewein, Taunusstein (DE); Ryan Michael West, West Chester, OH (US); Kevin Max Labitzke, West Chester, OH (US); Vincent Scott Stapp, Florence, KY (US); Emily Suzanne Allen, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 530 days.

(21) Appl. No.: 15/838,413

(22) Filed: Dec. 12, 2017

(65) Prior Publication Data

US 2018/0168894 A1     Jun. 21, 2018

Related U.S. Application Data

(60) Provisional application No. 62/435,934, filed on Dec. 19, 2016.

(51) Int. Cl.
| | | |
|---|---|---|
| *A61F 13/84* | (2006.01) | |
| *A61L 15/46* | (2006.01) | |
| *A61F 13/539* | (2006.01) | |
| *A61F 13/49* | (2006.01) | |
| *A61L 15/28* | (2006.01) | |

(Continued)

(52) U.S. Cl.
CPC .... *A61F 13/8405* (2013.01); *A61F 13/49007* (2013.01); *A61F 13/539* (2013.01); *A61L 15/18* (2013.01); *A61L 15/28* (2013.01); *A61L 15/46* (2013.01); *B01J 20/18* (2013.01); *B01J 20/2805* (2013.01); *A61F 2013/49092* (2013.01);

(Continued)

(58) Field of Classification Search
CPC .............. A61F 13/51113; A61F 13/539; A61F 13/8405; A61F 2013/51076; A61F 2013/5109; A61F 2013/5395; A61F 2013/8408; A61F 2013/8423; A61L 15/46
See application file for complete search history.

(56) References Cited

U.S. PATENT DOCUMENTS

| | | |
|---|---|---|
| 3,860,003 A | 1/1975 | Buell |
| 5,221,274 A | 6/1993 | Buell et al. |

(Continued)

FOREIGN PATENT DOCUMENTS

| | | |
|---|---|---|
| EP | 0677244 | 10/1995 |
| EP | 0811387 | 12/1997 |

(Continued)

OTHER PUBLICATIONS

International Search Report, PCT/US2017/065739, dated Mar. 28, 2018, 16 pages.

*Primary Examiner* — Catharine L Anderson
(74) *Attorney, Agent, or Firm* — C. Brant Cook; Kathleen Y. Carter

(57) ABSTRACT

Absorbent articles with substantially cellulose-free cores with zeolites.

19 Claims, 9 Drawing Sheets

(51) Int. Cl.
  *A61L 15/18* (2006.01)
  *B01J 20/18* (2006.01)
  *B01J 20/28* (2006.01)

(52) U.S. Cl.
  CPC .............. *A61F 2013/5395* (2013.01); *A61F 2013/8423* (2013.01)

(56) References Cited

U.S. PATENT DOCUMENTS

| | | | |
|---|---|---|---|
| 5,554,145 A | 9/1996 | Roe et al. | |
| 5,569,234 A | 10/1996 | Buell et al. | |
| 5,580,411 A | 12/1996 | Nease et al. | |
| 5,599,335 A | 2/1997 | Goldman et al. | |
| 5,700,254 A | 12/1997 | McDowall et al. | |
| 6,004,306 A | 12/1999 | Robles et al. | |
| 6,667,424 B1 * | 12/2003 | Hamilton | A61F 13/15 604/360 |
| 8,273,367 B2 * | 9/2012 | Pesce | A61L 15/20 424/400 |
| 2008/0057019 A1 * | 3/2008 | Collier | A61L 9/014 424/76.1 |
| 2008/0312622 A1 | 12/2008 | Hundorf et al. | |
| 2012/0277713 A1 | 11/2012 | Raycheck et al. | |
| 2015/0038929 A1 | 2/2015 | Van Malderen | |
| 2015/0080821 A1 | 3/2015 | Peri et al. | |
| 2017/0056257 A1 | 3/2017 | Nishikawa et al. | |
| 2017/0267618 A1 * | 9/2017 | Sookraj | C07C 51/50 |

FOREIGN PATENT DOCUMENTS

| | | |
|---|---|---|
| EP | 1447066 | 8/2004 |
| EP | 2444046 | 4/2012 |
| EP | 2851048 | 3/2015 |
| WO | WO9111977 | 8/1981 |
| WO | WO 95/10996 | 4/1995 |
| WO | WO 95/11652 | 5/1995 |
| WO | WO9746192 | 12/1997 |
| WO | WO 2000/59430 | 10/2000 |
| WO | WO 02/067809 | 9/2002 |
| WO | WO 2012/052172 | 4/2012 |

* cited by examiner

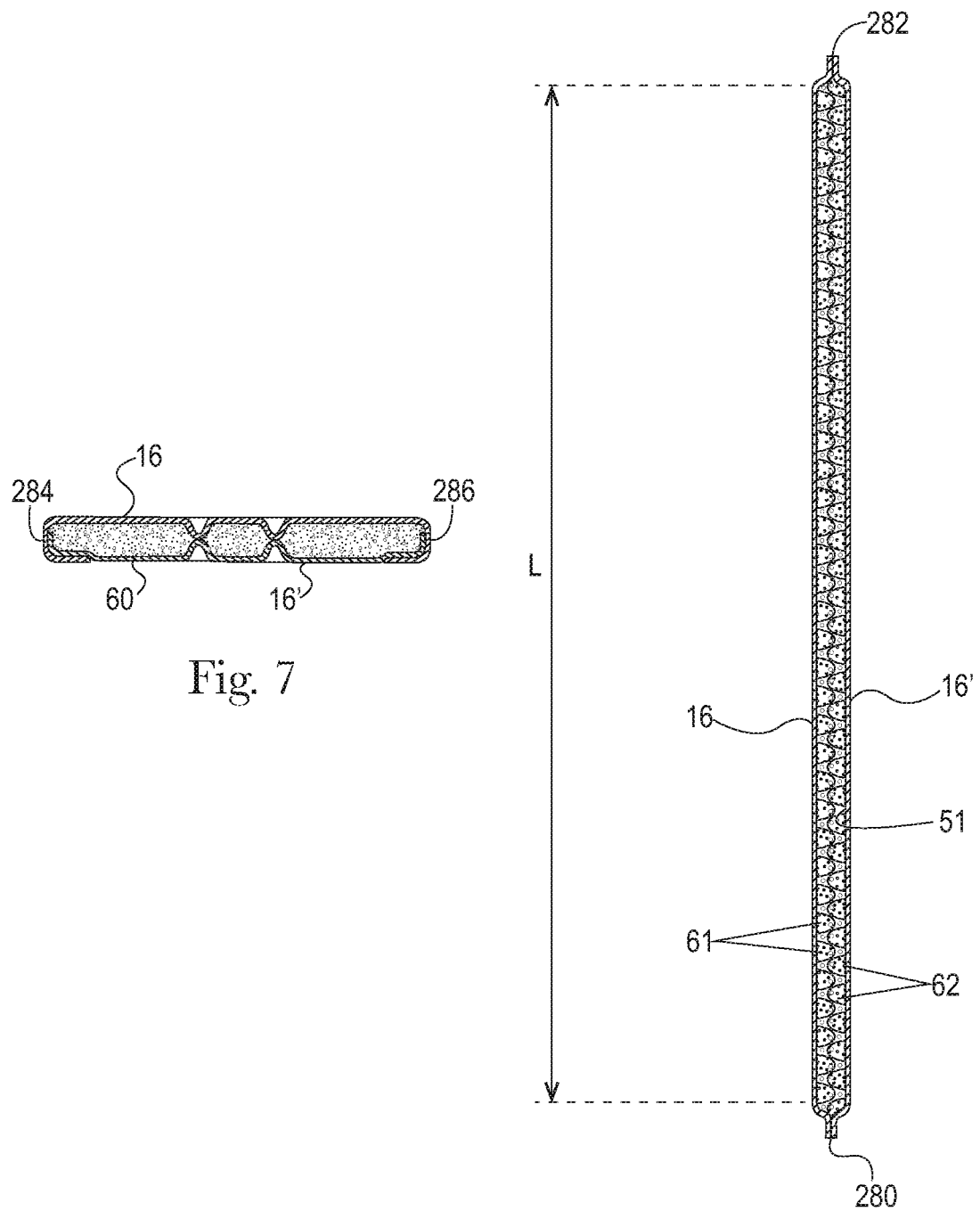

ARTICLE WITH ZEOLITES

CROSS REFERENCE TO RELATED APPLICATION

This application claims the benefit of U.S. Provisional Application No. 62/435,934, filed on Dec. 19, 2016.

FIELD OF THE INVENTION

The present invention relates to absorbent articles comprising zeolites and methods of making and using same.

BACKGROUND OF THE INVENTION

Unscented or low scented products are desired by consumers as they may be considered more natural and discreet than scented products. Manufacturers of unscented or low scented products for controlling odors rely on odor reduction ingredients or other technologies (e.g. filters) to reduce malodors. Activated carbon, metal organic frameworks (MOFs), silicas, aluminas and clays can also be used to adsorb odor molecules. Additionally, zeolites, or aluminosilicates, are known adsorbents that can be used to control unwanted odors. But though zeolites in general are known to adsorb odors, due to the variety of components in an absorbent article, it can be difficult to understand what particular zeolite or combination of zeolites will work effectively to neutralize the specific odors in an absorbent article. Plus there are considerations of cost and ease of manufacturing. Therefore, there is a continuing need for particular odor adsorbing materials and particular zeolites that can control or reduce unwanted odors while maintaining an attractive appearance of the product.

SUMMARY OF THE INVENTION

A disposable absorbent article having a longitudinal centerline and a lateral centerline, a front waist region with a front waist edge, a rear waist region with a rear waist edge, a crotch region disposed between said front and rear waist regions and two spaced apart longitudinal side edges joining said front waist edge to said rear waist edge and comprising an assembly of components including a topsheet, a backsheet, and an absorbent core therebetween, said absorbent core being substantially free of cellulose fibers and comprising zeolites.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting examples of the disclosure taken in conjunction with the accompanying drawings, wherein:

FIG. 7 is a cross-sectional view of the absorbent core taken about line 7-7 of FIG. 6 in accordance with the present disclosure;

FIG. 8 is a cross-sectional view of the absorbent core taken about line 8-8 of FIG. 6 in accordance with the present disclosure;

DETAILED DESCRIPTION OF THE INVENTION

Definitions

Figure 1:
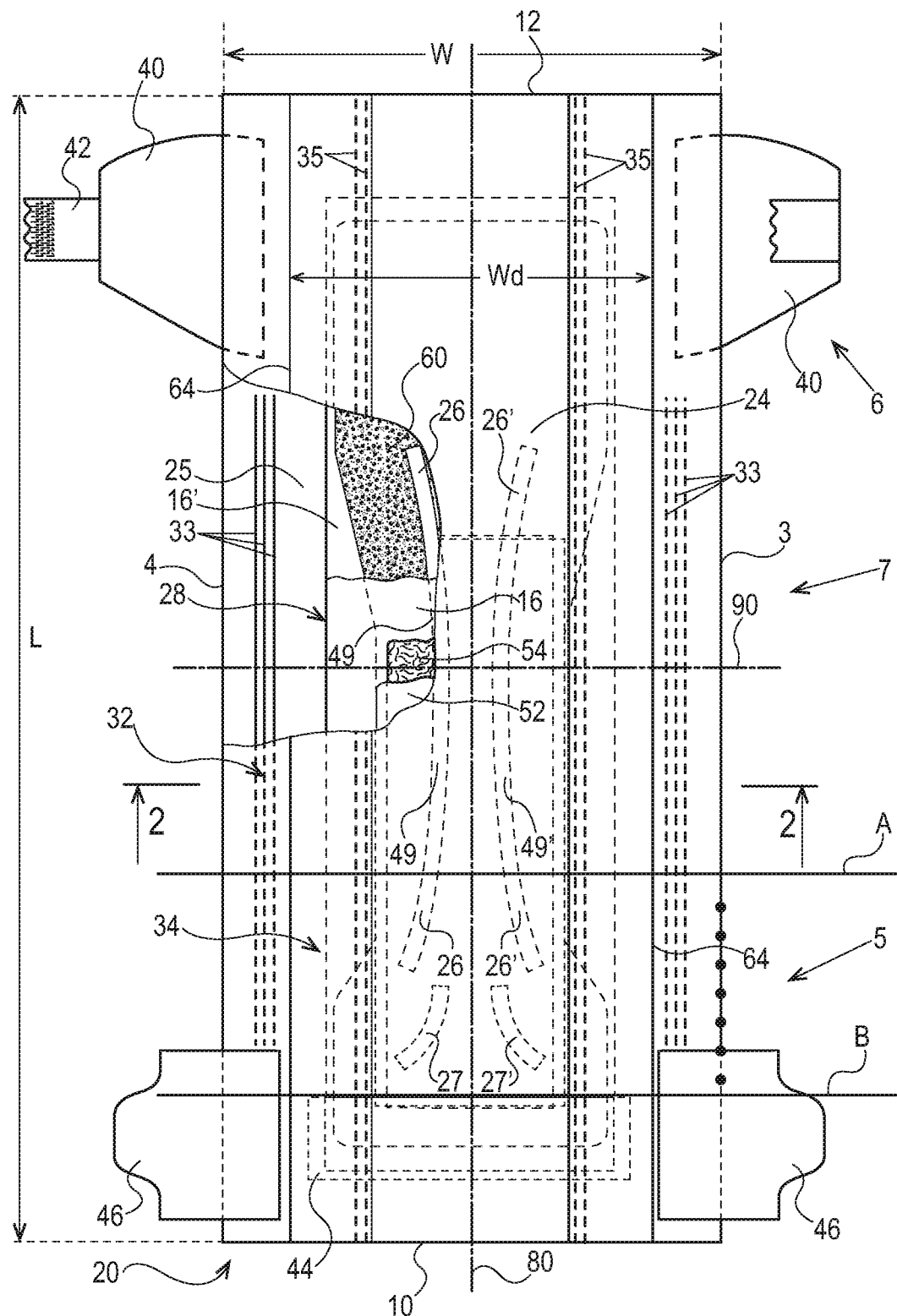
FIG. 1 is a top view of an absorbent article with some layers partially removed in accordance with the present disclosure.

The term "absorbent article, as used herein, refers to disposable devices such as infant, child, or adult diapers, sanitary napkins, adult incontinence products, pant-style diapers, training pants, diaper inserts, and the like which are placed against or in proximity to the body of the wearer to absorb and contain the bodily exudates (e.g., urine and BM) discharged from the body. Typically, these articles comprise a topsheet, backsheet, an absorbent core, optionally a liquid management system (LMS), and typically other components, with the absorbent core normally placed at least partially between the backsheet and the LMS (if provided) or between the topsheet and the backsheet. The absorbent articles of the present disclosure will be further illustrated in the below description and in the Figures in the form of a taped diaper. Nothing in this description should be, however, considered to limit the scope of the claims. As such the present disclosure applies to any suitable form of absorbent articles (e.g., training pants, taped diapers, adult incontinence products-in either taped or pant forms, sanitary napkins).

"Adhesive" refers to compositions comprising one or more thermoplastic polymers and typically one or more tackifier resins and a rheology modifier or plasticizer. Adhesives may contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

As used herein "consumer product" means baby care and/or feminine care products or devices intended to be used or consumed in the form in which it is sold, and not intended for subsequent commercial manufacture or modification. Such products include but are not limited to diapers, bibs, wipes; skin care including application of creams, lotions, and other topically applied products for consumer use; tampons and/or feminine napkins.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

As used herein, "malodor" refers to compounds generally offensive or unpleasant to most people.

As used herein, "neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Neutralization is distinguishable from odor masking or odor blocking by a change in the malodorous compound, as opposed to a change in the ability to perceive the malodor without any corresponding change in the condition of the malodorous compound. Malodor neutralization provides a sensory and analytically measurable (e.g. gas chromatograph) malodor reduction. Thus, if a malodor reduction composition delivers genuine malodor neutralization, the composition will reduce malodors in the vapor and/or liquid phase.

The term "nonwoven web", as used herein, means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter (g/m$^2$ or gsm).

The terms "join", "joined" "joining", "bond", "bonding", "bonded", "attach", "attached", or "attaching" as used herein, encompasses configurations whereby an element is directly secured to another element by affixing the element directly to the other element, and configurations whereby an element is indirectly secured to another element by affixing the element to intermediate member(s) which in turn are affixed to the other element.

As used herein, "odor masking" refers to the ability of a compound with a non-offensive or pleasant smell that is dosed such that it limits the ability to sense a malodorous compound. Odor-masking may involve the selection of compounds that coordinate with an anticipated malodor to change the perception of the overall scent provided by the combination of odorous compounds.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50 percent, at least about 100%, or at least about 125%, without experiencing catastrophic failure.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Zeolites

Zeolites are composed of the elements silicon, aluminum, oxygen and occasionally other more rare metals. The raw materials that go into making zeolites are digested with strong base to form soluble silicate and soluble aluminate. For the simplest zeolites (such as A, X, Y, and higher alumina containing ZSM-5s), the soluble forms are mixed in a specific ratio with water and acid (as necessary to adjust the pH) and allowed to crystallize at a set temperature for a set time. For more complex zeolites such as low alumina ZSM-5, an organic templating agent is added in this step and allowed to crystallize. After filtering, the zeolites are calcined or dried at high temperatures. This calcination removes bound water and in the case of ZSM-5, burns off the organic templating agent. Typically, the crystals as formed are quite small and it may be necessary to increase the particle size. There are two typical processes for increasing size, agglomeration to produce beads or spheres and extrudation to produce cylindrical pellets. Both these process typically require the use of an additional component such as a binder to aid in the agglomeration or extrusion and additional base. There are several types of additional components with alumina and silica as common examples along with clay (which can have iron in it and turn the samples brown).

There are currently over 220 different types of recognized zeolite crystal structures. All of these structures are made up of different configurations of the same building block structures, and each is identified by a three letter code that defines the base crystal structure. Two examples, Y type and ZSM-5, are coded FAU for Faujasite and MFI for Mordenite Framework Inverted, respectively. The X type zeolite is not actually a different structure, but is the same structure, FAU as the Y type.

The most prominent difference amongst different classes of zeolites for adsorption purposes is the size of the pores formed in the crystals. The size of the pores is named for the number of tetrahedral atoms or T atoms (Si, Al, Ti) that are present. In addition to these T atoms, oxygen atoms are also present in between each T atom. As the number of atoms in the ring becomes larger, the diameter of the pore becomes larger.

The smallest rings encountered for practical purposes have 8 T. These pores are small, but are able to pick up water, and small gaseous molecules like CO and $H_2S$. The pores of this zeolite are typically from 3 to 5 Å (angstroms). The most common zeolite this size is LTA (Linde Type A). The next largest rings consist of 10 T. Although several examples exist, the most common is ZSM-5, also known as MFI. This material has two different channels that intersect each other. The diameter of the pore created by the 10 Si is around 5-5.6 Å. This allows for fairly specific adsorption and rejection based on size.

The final ring size that is typically encountered has 12 T in it. There are multiple examples of this structure, as it is more common than the 10-membered rings. While a 12-membered ring can reject very large molecules, most volatile organic compounds, for example, will easily fit into the pores. As a general rule, a larger pore will result in less interaction with the adsorbed molecule and therefore a weaker overall binding. So while these structures can adsorb more, they hold on less tightly. Three of the more common 12 T rings structures are given below with some description of each.

One, mordenite (MOR) framework can be found both naturally and synthetically. Two, Beta (BEA), is one of the first zeolites discovered (along with A, X and Y). This crystal structure contains pores of different sizes. This zeolite is more difficult to make than A or Y, often requiring seeding and a long crystallization time. And three, Y Zeolite (Faujasite, FAU), are the second most heavily produced zeolite (behind A). This zeolite has the widest diameter pore widely available. This zeolite also features a large cage structure of 12-13 Å across and is accessible through the pores. As the size of the molecules being adsorbed becomes bigger, they physically cannot fit into the pores of the zeolites.

The framework crystal structure sets the overall pore, distance between pores, the existence or absence of open cages within the structure and the overall repeat unit. Other factors, specifically the aluminum content, along with the corresponding counter ion that is necessary to compensate for the aluminum make a very large difference in the accessibility of the pores and the hydrophobicity of the zeolite. Together all of these factors determine which molecules can physically enter the structure, and also determine the strength by which they are retained both inside the pores and on the surface.

Si with 4 oxygen bonds is the most abundant T atom found in zeolites, although most zeolites have some aluminum incorporated into them. Since aluminum has a strong preference to reside as a +3 cation (i.e. only make 3 bonds), when it is forced into a system where it is required to make 4 bonds (in Si—O network) it obtains an additional negative charge that must be countered with a cation. The mismatch causes a negative charge that is localized over the oxygen and aluminum atoms. As zeolites are made in sodium derived basic solutions, the counter ion that is typically present is sodium as a positive cation. The positive nature of the sodium causes attraction of water around the cation. By drying the zeolite at high temperature (well over 200° C.), this water can be removed, however the zeolite will begin immediately to adsorb water from the surrounding air if it is not kept under water free (no humidity) conditions.

The location of the Al in zeolites is not limited to the pores, but also exists on the surface. As the amount of Na increases, the amount of water that remains bound to a zeolite also increases. This water can block absorption of volatile organic compounds (VOC's) into channels. Removal of Na can be accomplished with ion exchange, that is, exchange of the Na ions for different cations. For adsorbants, the most common exchange cation is $NH_4OH$. This leaves the zeolite with $NH_4^+$ as a counter ion instead of sodium. Subsequent heating to 400-500° C. enables $NH_3$ to leave the structure and $H^+$ to remain as the counter ion. The H-form is much less hydrophilic than the Na form. In addition, the total amount of moisture contained within the zeolite decreases. This allows less blockage of the pores and greater absorption of VOC molecules.

The initial Na content of a zeolite is set by the initial content of Al. A zeolite with a low initial silica to alumina ratio (SAR, $SiO_2/Al_2O_3$), such as Y (initial SAR=5-6), has a high initial content of Na, (10-13 wt %). The initial SAR of Y-type is capped at 5-6, and cannot go higher. This is due to the crystallization of Y from solution. Attempts to change the amount of silicate and aluminate in the solution before crystallization will result in either Y at SAR=5-6 or a different crystal structure being formed. If reduction of the Al content is required (dealumination), this can be accomplished by reacting the Na form with steam at elevated temperatures. The water reacts with the $Na^+$ to form NaOH; which then attacks the Si—O—Al bonds to make SiOH+ Na—O—Al. After all of the Al bonds are broken, the sodium aluminate can be removed from the framework, thus reducing the Al content and increasing the SAR. The resulting materials then need to be recalcined. If a higher SAR is desired, the process can be repeated.

For ZSM-5 zeolites, the initial SAR can be changed depending upon the ratio of the components in the crystallization step. For SAR up to around 50, a direct method of crystallization is available. If a SAR above 50 is desired (can go to infinity, pure Si), then a templating agent such as tetrapropyl amine bromide is needed. In this later case, the zeolite must then be calcined at 650° C. after crystallization to remove the templating agent.

For absorbent articles, the particle size for direct incorporation of zeolite particles into the absorbent core of the article may be from about 200 µm to about 800 µm. In some embodiments, the zeolite particle size may be from about 250 µm, 300 µm, 350 µm, 400 µm, 450 µm, or 500 µm to about 600 µm, 650 µm, 700 µm, 750 µm, or 800 µm, in any combination. In order to achieve this dimension, the zeolite crystals (0.2-1 µm) may be agglomerated or extruded (often with an additional component or binder such as silica or alumina as described previously).

There are tens to hundreds of different amorphous structures based on the same elements as zeolites. Amorphous in this context refers to the fact that these materials do not have repeating crystalline domains like zeolites. There are numerous ways to either make or modify these materials. The surface area can range from extremely low like solid quartz or alumina chips/sand (less than 0.1 $m^2/g$) to very high, about 250 $m^2/g$. These very high surface area materials contain macropores (greater than 50 nm), mesoporous pores (2-50 nm), and micropores (less than 2 nm). Due to the high surface area and presence of various pore sizes, these materials can adsorb odor molecules. Obviously with a very large range of pores and surface area, comes a very large range of absorption capabilities. While some materials will not take up any VOC's, others can provide a very noticeable benefit.

In a context of zeolites, these materials can be used as a binding agent when increasing the particle size. In the context of agglomeration, several points can be made about these materials and their impact on the final material. First, the additional component or binders (silica, alumina, clay) can adsorb some VOC's with a different affinity than zeolites. Second, although the affinity is often weaker than zeolites, they can still impact score and character. Third, the additional component or binder particle size is typically on the same order of magnitude or greater than the zeolite crystals.

The present inventors have discovered that each of the many odor-adsorbing materials and in particular each type of zeolite has its own profile of compounds that it adsorbs. In addition, in terms of consumer perception of odors, it is not necessary that each and every odor be reduced—it may be that the reduction of one type of compound or molecule in a particular absorbent article is sufficient to improve the consumer experience. But materials that can improve the odor of one type of absorbent article may not necessarily have the same effect on a differently-structured absorbent article.

Faujasites have the largest pore size in large volume zeolites at 7.4 Å. They also possess a cage that with a diameter of 12-13 Å. These zeolites can only be made with a range of $SiO_2/Al_2O_3$ of about 1 to 6. Because of the need to charge balance the high level of Al (+3), these materials start with a fairly high Na content (13-10% by weight).

The presence of Na has a very large influence on the efficacy of absorption. Data shows that the relative absorption profile of Y zeolites at constant $SiO_2/Al_2O_3$ changes as the amount of Na is reduced from the initial 13 wt % to close to 0. As the Na is removed, more and more species are adsorbed at higher amounts.

In addition to exchanging the Na out of the FAU framework, the ratio of $SiO_2$ to $Al_2O_3$ (SAR) can also be changed by an additional process of dealumination. However, both GCMS analysis (Gas chromatography—mass spectrometry) and sensory analysis indicate that changing the SAR for Y zeolites, for example, may have little impact on adsorption of VOC's. Also, the removal of alumina can add substantial cost to the material compared to the removal of Na. The GCMS analysis looks at the removal of certain compounds in a sealed jar that contains a representative portion of an article at a set time and loading of odor-adsorbing material relative to a blank.

Because of how MFI is made, the lowest SAR that is obtainable is around 25. At this ratio, there is much less Na present than in FAU, with a theoretical maximum at 100% crystallinity of 2.4% Na. At higher SAR there is even less Na present, so a study on Na content is impractical (at SAR=100, Max Na=0.6%). Also unlike FAU, the SAR can be much higher in MFI frameworks with a limit of infinity (i.e. no aluminum).

The MFI framework has much smaller pores than the FAU framework, and the adsorption profile is quite different than FAU, as are the odor descriptors. For example, the MFI framework may not adsorb certain large diameter VOC's very effectively. While they may be able to bind to the exposed outer surface, they cannot be taken up inside the MFI structure.

The mordenite crystal structure can be obtained in both a natural (mined) and a synthetic form. The natural form tends to be quite hydrophilic with cations other than sodium, such as iron. The synthetic form can be made with varying SAR and Na content, just like the previously discussed zeolites. Mordenite (MOR) has a pore size of 6.5-7.0 Å that is smaller than FAU (7.4 Å), but larger than MFI (5.1-5.6 Å). For a high sodium, low SAR MOR, the adsorption is notably worse than a lower sodium high SAR. This trend is consistent with the observations for FAU, and the same conclusions can be drawn, namely lower sodium and high SAR perform better. As previously discussed, the FAU may have difficulty adsorbing the small molecules with lower functionality, while the MFI had difficulty adsorbing the large size excluded molecules. MOR seems to have both of these difficulties and does not adsorb either the small low functional molecules or the large bulky molecules. However, MOR does show good adsorption of all the other molecules across the board.

An odor-adsorbing material must be efficacious for a period just after production and lasting several months. Therefore an odor-adsorbing material must be able to hold onto the adsorbed compounds and not release them at a later time, a phenomenon called blooming. For zeolites, VOCs that are strongly adsorbed by a given structure are not released with time. This trend is observable for both MFI and FAU structures.

Mixtures of two different odor-adsorbing materials have the potential of surpassing either of the individual odor-adsorbing materials. Reasons for this include the following: First, there is ample capacity for adsorption in zeolites; second, certain molecules are highly adsorbed by different zeolites even at low loadings of zeolites; and third, molecules not adsorbed by one type of odor-adsorbing material (FAU, for example) are strongly adsorbed by another (MFI for example) and vice versa.

For example, data shows that 300 mg of total zeolite added as 150 mg of HY plus 150 mg of ZSM-5 produced greater VOC reduction than either 300 mg of HY or 300 mg of ZSM-5. In total, this material removed around 85% of all VOC, while either individual removed less. In sensory studies, a similar trend is noted. When two odor-adsorbing materials are combined, the resulting profile of the mixture is better than either of the two individual components. This is observed for a Y zeolite mixed with alumina and also holds for mixtures of two zeolites.

The present invention may include zeolites mixed with silicas, or may have silicas alone as an odor control composition. Silica, i.e. silicon dioxide $SiO_2$, exists in a variety of crystalline forms and amorphous modifications, any of which are suitable for use herein. Silicas tend to have a high surface area, and the silica may be in agglomerated form. The silica may be in a highly purified form such that it contains at least about 90%, about 95%, or even about 99% silicon dioxide. The silica may be silica gel having 100% silica content. Alternatively, the silica may be provided from other sources such as metal silicates including sodium silicate.

The silica may be used alone or may be mixed with one or more types of zeolites. The ratio of silica to zeolite may be from about 1:3, about 1:2, about 1:1, about 2:1, about 3:1, about 4:1, or about 5:1.

In general, the amount of zeolites, silicas, and/or blends of both or either may be from about 0.05 g to about 1.2 g per article. In some embodiments, the amount of zeolite, silica, or blend may be from about 0.05 g to about 1.0 g, from about 1.0 g to about 1.2 g, from about 0.15 g to about 1.0 g, from about 0.2 g to about 0.8 g, from about 0.3 g to about 0.7 g, from about 0.4 g to about 1.0 g, from about 0.15 g to about 0.3 g, from about 0.10 g to about 0.3 g, or from about 0.05 g to about 0.3 g.

Table 1 below shows exemplary zeolites that may be used, individually or as mixtures, in the present invention. The table lists zeolites with exemplary SAR and sodium content expressed as $Na_2O$. Also included are exemplary amounts of zeolite and/or silica used in a cellulose-free absorbent core in an absorbent article.

TABLE 1

| | Adsorbent Type | Base Description | Product Name, Supplier | grams per article |
|---|---|---|---|---|
| 1 | Y Zeolite | SAR > 5.5 Na < 1% | CBV 901 or 88Y, PQ Silica | 0.05-1.0 |
| 2 | ZSM-5 Zeolite | 30 < SAR < 100 Na < 1% | CBV 8014 or 14Z, PQ Silica | 0.05-1.0 |
| 3 | Mixture of Y and ZSM-5 Zeolites | SAR > 3.5 Na < 2% 50:50 mixture of ZSM-5:Y | ZD 16010 or 19B, PQ Silica 40% Y (CBV-400, PQ Silica) 40% ZSM-5 (CBV-8014, PQ Silica) 20% binder, PQ Silica | 0.05-1.0 |
| 4 | Mixture of MOR, Y and ZSM-5 Zeolites | SAR > 3.5 Na < 2% | 8% MOR (Zeoflair 810, Zeochem) 21.6% Y (UY-22, Huaxin) 50.4% ZSM 5 (ZSM-5-5B, Huaxin) 20% binder, Zeochem | 0.05-1.0 |
| 5 | Silica | Silica | Zeofree 5841, J M Huber | 0.05 to 1.0 |

TABLE 1-continued

| | Adsorbent Type | Base Description | Product Name, Supplier | grams per article |
|---|---|---|---|---|
| 6 | Mixture of Silica and 1 Zeolite | 2:1 ratio of Silica:ZSM-5-5B | 67% Silica (5841, J M Huber) 33% ZSM-5 (ZSM-5-5B, Huaxin) | 0.05 to 1.0 |
| 7 | Mixture of Silica and 2 Zeolites | 3:1:1 ratio of Silica:ZSM-5:Y | 60% Silica (5841, J M Huber) 20% ZSM-5 (ZSM-5-5B, Huaxin) 20% Y (USY-0, Huaxin) | 0.05 to 1.0 |

As examples, an absorbent article may have a substantially cellulose-free absorbent core, with about 0.05 g to about 1.0 g of any of the materials in rows 1-7 of Table 1 inside the core. Specifically, an article with a substantially cellulose-free absorbent core may have about 0.15 g of a 1:1 mixture of Y and ZSM-5 zeolites mixed with 20% of an alumina binder, such as described in row 3 in Table 1, in the form of an agglomerated pellet.

The difference in zeolite materials can be broken out according to 1) Na content 2) SAR, 3) pore size (with Y being 7-9 Å and ZSM-5 being 5-6 Å). An initial group of Y zeolites may all have a SAR of 5.2 but different levels of Na. As the Na content is lowered, the zeolites become much less hydrophilic. In GCMS, decreased Na corresponds to a much greater absorption of VOC's while in sensory tests it corresponds with a drop in average sensory score. Further removal of Na at the same SAR may provide slightly more VOC removal in GCMS. The Y zeolites at very low Na level (less than 0.1%) may have a higher SAR due to dealumination.

For ZSM-5 samples, the lowest SAR is around 25 while still performing well in sensory tests. However, increasing the SAR to about 50 to about 80 allows initially for a better sensory score.

For hydrophobicity, for FAU, MFI, or mixtures of the two types, as the hydrophobicity increases, the adsorption of VOC's improves. Also notable is that mixtures perform better than either of the two components alone.

In summary, zeolites with low Na and middle hydrophobicity may provide good odor adsorption. The VOC's taken out by large pore zeolites (7.4 Å) are different than those taken out by medium to small pore zeolites (5.3-5.5 Å). The character profile of these two materials are also different. The two pore sizes can complement each other when mixed together both in the total VOC removed and in overall sensory scores.

The articles of the present invention may have absorbent cores that are substantially cellulose-free or that may be cellulose-free, which comprise zeolites. In some embodiments, the zeolites may be selected from the group consisting of a FAU framework, a MFI framework, a MOR framework, and mixtures thereof. In some embodiments, the framework may include a FAU framework, alone or with other frameworks, and the sodium content, expressed as $Na_2O$, may be below about 15%, below about 10%, below about 5%, below about 2%, below about 1%, below about 0.5%, or below about 0.1% by weight of the FAU framework. Similarly, embodiments may comprise a MFI framework wherein the sodium content, expressed as $Na_2O$, may be below about below about 5%, below about 2%, below about 1%, below about 0.5%, or below about 0.1% by weight of the MFI framework. And embodiments may comprise a MOR framework, alone or with other frameworks, wherein the sodium content, expressed as $Na_2O$, may be below about 10%, below about 5%, below about 2%, below about 1%, below about 0.5%, or below about 0.1% by weight of the MOR framework. The FAU, MFI, and MOR frameworks, or any other framework, in any embodiment may also have a silica to alumina ratio. For the FAU framework, the silica to alumina ratio may be from about 3 to about 5, from about 4 to about 5, from about 4 to about 6, greater than about 4, or greater than about 5 or from about 4 to about 100, or from about 5 to about 100. For the MFI framework, the silica to alumina ratio may be from about 25 to about 500, or from about 50 to about 400, or less than about 500, or greater than about 25. For the MOR framework, the silica to alumina ratio may be greater than about 10, or may be greater than about 15, or may be from about 10 to about 50.

In some embodiments, a zeolite may be mixed with an additional component, such as silica, alumina, clay, silica-aluminate, or other metal oxide, or mixtures thereof. In some embodiments, the zeolite or mixture of zeolites may be granulated, agglomerated, or extruded to increase the particle size. The particle size distribution of granulated zeolites may be from about 100 microns to about 850 microns. In some embodiments, the particle size distribution of granulated zeolites may be from about 80, about 90, or about 100 microns to about 600, about 700, about 800, about 850, about 900, or about 1000 microns.

The zeolites of the present invention may be a mixture of different frameworks. In some embodiments, the zeolites may comprise a mixture of FAU and MFI frameworks. In some FAU and MFI mixtures, the FAU framework may comprise from about 10% to about 90% by weight of the zeolite, and the MFI may comprise from about 10% to about 90% by weight of the zeolite. In other FAU and MFI mixtures, the FAU framework may comprise from about 25% to about 75% by weight of the zeolite and the MFI may comprise from about 25% to about 75% by weight of the zeolite. Some embodiments may be mixtures of MOR and MFI frameworks. In some MOR and MFI mixtures, the MOR framework may comprise from about 10% to about 90% by weight of the zeolite and the MFI may comprise from about 10% to about 90% by weight of the zeolite. In other embodiments, there may be mixtures of FAU, MFI, and MOR frameworks. The FAU, MFI, and MOR mixtures may comprise from about 10% or 20% to about 70% or 90% of FAU, from about 10% or 20% to about 70% or 90% of MFI, and about 0% or 10% to about 10% or 90% MOR, by weight of the zeolite.

Article

Figure 2:
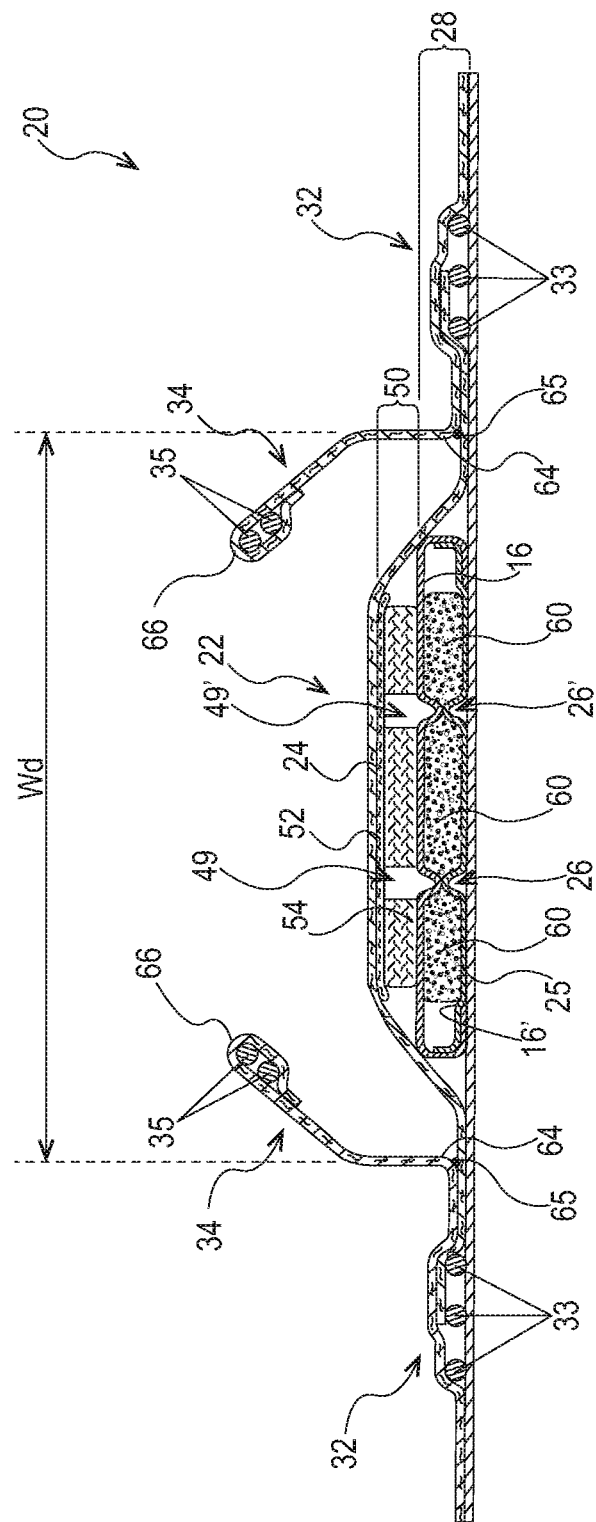
FIG. 2 is a cross-sectional view of the absorbent article taken about line 2-2 of FIG. 1 in accordance with the present disclosure.
Figure 3:
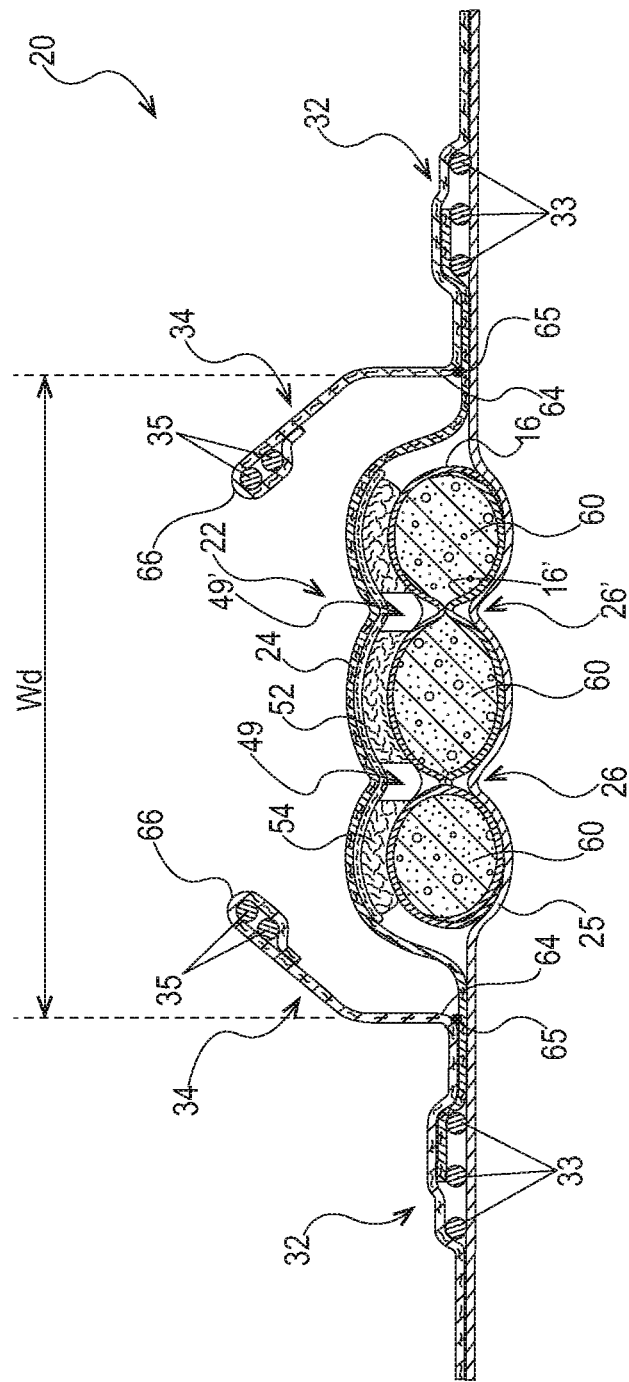
FIG. 3 is a view of the absorbent article of FIG. 2 where the absorbent article has been at least partially loaded with fluid in accordance with the present disclosure.

An example absorbent article 20 according to the present disclosure, shown in the form of a diaper, is represented in FIGS. 1-3. FIG. 1 is a plan view of the diaper, in a flat-out state, wearer-facing surface toward the viewer, with portions of the structure being cut-away to more clearly show the construction of the diaper. This diaper is shown for illustration purpose only as the present disclosure may be used for making a wide variety of diapers and other absorbent articles.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise a liquid management system ("LMS") 50 (shown in FIG. 2), which, in the example represented, comprises a distribution layer 54 and an acquisition layer 52 that will both be further discussed below. In various forms, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature and a front elastic waist feature, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. Together the front waist edge 10 and the rear waist edge form waist opening when the absorbent article 20 is donned on a wearer. The absorbent article 20 may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from the wearer-facing surface as illustrated FIG. 1. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width of the absorbent article 20 may be measured along the lateral axis 90 from the first side edge 3 to the second side edge 4. The absorbent article 20 may comprise a front waist region 5, a rear waist region 6, and a crotch region 7. The front waist region, the rear waist region, and the crotch region each define ⅓ of the longitudinal length of the absorbent article. Front and back portions may also be defined on opposite sides of the lateral axis 90.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 28 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' (see FIG. 8) for the top side and bottom side of the core.

The absorbent core 28 may comprises one or more channels, represented in FIG. 1 as the four channels 26, 26' and 27, 27'. Additionally or alternatively, the LMS 50 may comprise one or more channels, represented in FIGS. 1-3 as channels 49, 49'. In some forms, the channels of the LMS 50 may be positioned within the absorbent article 20 such they aligned with, substantially aligned with, overlap, or at least partially overlap, the channels of the absorbent core 28.

These and other components of the absorbent articles will now be discussed in more details.

Topsheet

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The topsheet 24 may be compliant, soft-feeling, and non-irritating to the wearer's skin. Further, at least a portion of the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, melt-blown, hydroentangled, or otherwise processed as is known in the art, in particular spunbond PP nonwoven.

Typical absorbent article topsheets have a basis weight of from about 5 gsm to about 50 gsm, from about 10 to about 35 gsm or from about 12 to about 30 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the bodily exudates absorbed and contained therein from soiling articles such as bedsheets and undergarments. The backsheet 25 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, bodily exudates from passing through the backsheet 25. Example breathable materials may include materials such as woven webs, nonwoven webs, composite materials such as film-coated nonwoven webs, microporous films, and monolithic films.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20.

Absorbent Core

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 28 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than about 30%, less than about 20%, less than about 15% or less than 10% weight percent of natural or synthetic fibers or cellulose, less than 5% weight percent, less than 3% weight percent, less than 2% weight percent, less than 1% weight percent, or may even be substantially free of, or free of, cellulose or natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 30%, 25%, 20%, 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

Figure 4:
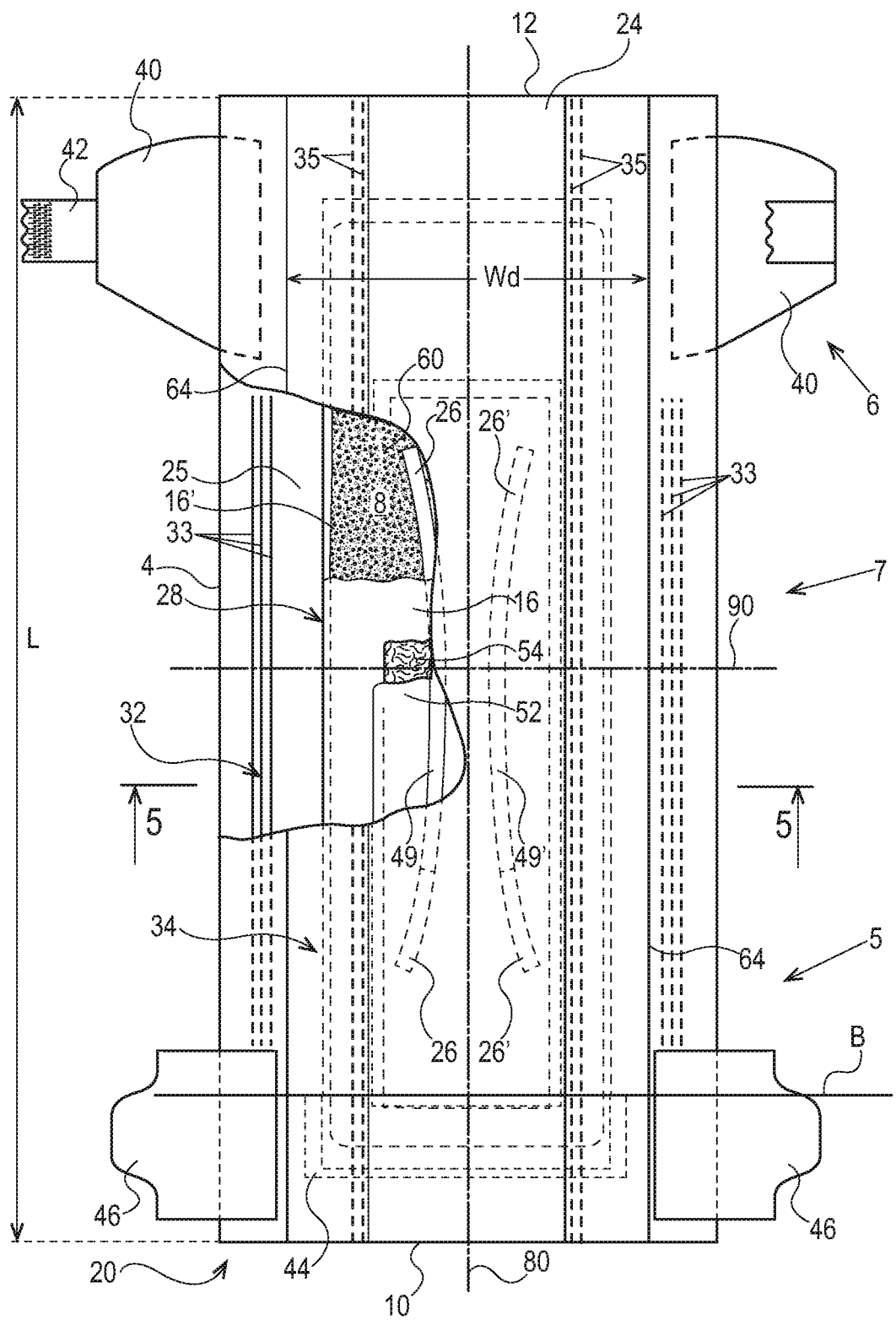
FIG. 4 is a top view of another absorbent article with some layers partially removed in accordance with the present disclosure.
Figure 5:
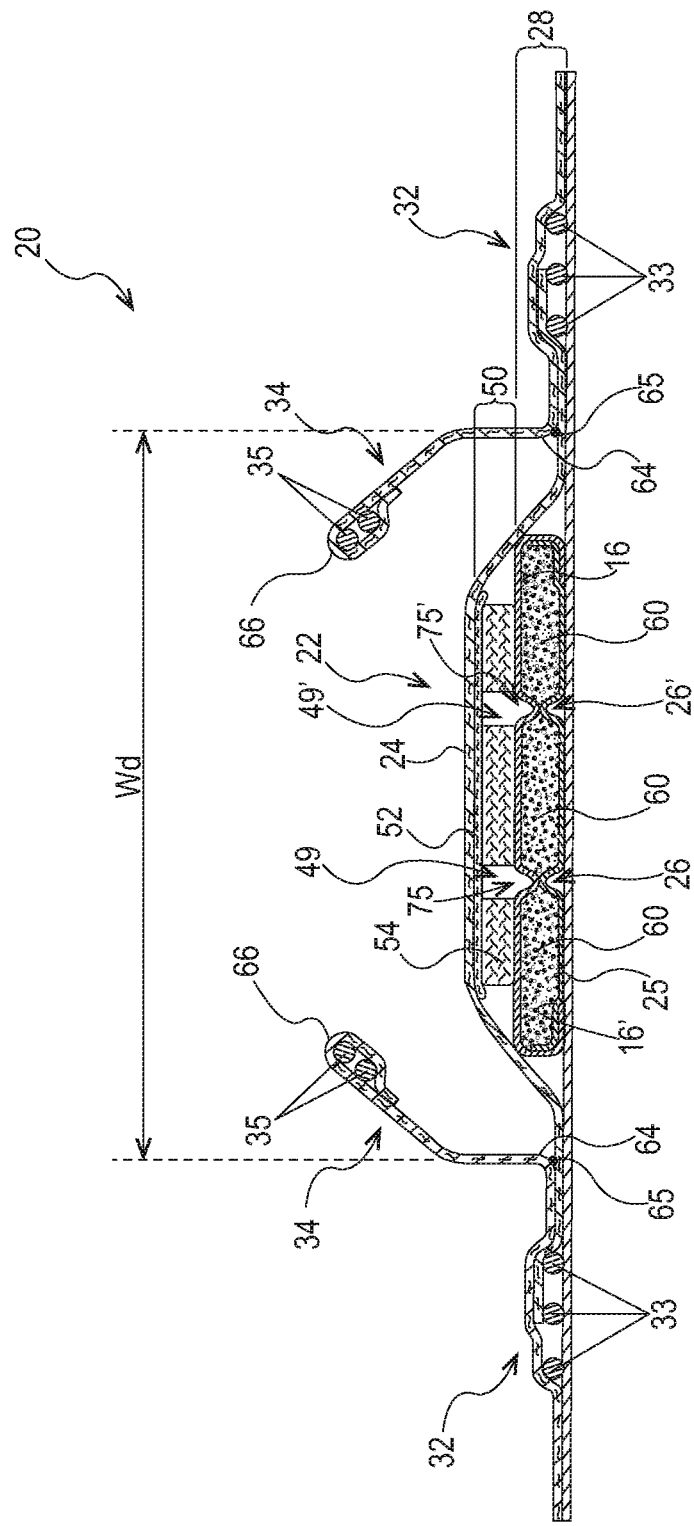
FIG. 5 is a cross-sectional view of the absorbent article taken about line 5-5 of FIG. 4 in accordance with the present disclosure.
Figure 6:
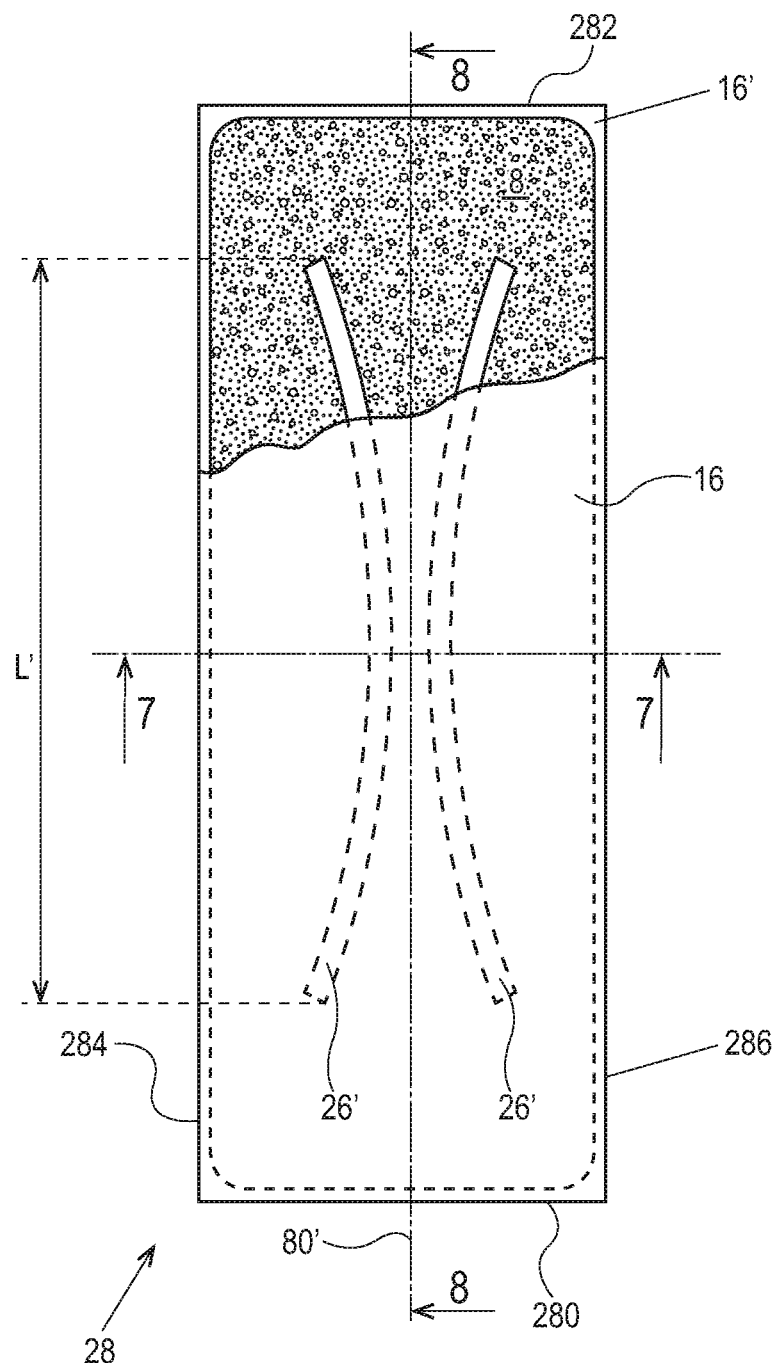
FIG. 6 is a top view of an absorbent core of the absorbent article of FIG. 4 with some layers partially removed in accordance with the present disclosure.

The example absorbent core 28 of the absorbent article of FIGS. 4 and 5 is shown in isolation in FIGS. 6-8. The absorbent core 28 may comprise a front side 280, a rear side 282, and two longitudinal sides 284, 286 joining the front side 280 and the rear side 282. The absorbent core 28 may also comprise a generally planar top side and a generally planar bottom side. The front side 280 of the core 28 is the side of the core 28 intended to be placed towards the front waist edge 10 of the absorbent article. The core 28 may have a longitudinal axis 80' corresponding substantially to the longitudinal axis 80 of the absorbent article, as seen from the top in a planar view as in FIG. 1. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 16, 16' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example.

The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a "T," "Y," "hour-glass," or "dog-bone" shapes are also within the scope of the present disclosure.

Channels in the Absorbent Core

The absorbent material deposition area 8 may comprise at least one channel 26, which is at least partially oriented in the longitudinal direction of the absorbent article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may be circular, oblong, or be in the shape of a variety of other closed polygons. The channels may be formed in various ways. For example, the channels may be formed by zones within the absorbent material deposition area 8 which may be substantially free of, or free of, absorbent material, in particular, SAP. In addition or alternatively, the channels may also be formed by continuously or discontinuously bonding the top side of the core wrap to the bottom side of the core wrap through the absorbent material deposition area 8. The channels may be continuous or intermittent. The liquid management system 50, or another layer of the absorbent article, may also comprise channels, which may or not correspond to the channels of the absorbent core, as described in more detail below.

The absorbent core 28 may comprise more than two channels, for example, at least 3, at least 4, etc. Shorter channels may also be present, for example in the rear waist region 6 or the front waist region 5 of the core as represented by the pair of channels 27, 27' in FIG. 1 towards the front of the absorbent article 20. The channels may comprise one or more pairs of channels symmetrically arranged, or otherwise arranged relative to the longitudinal axis 80 or the lateral axis 90.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the a backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Absorbent cores and/or LMSs without any channels are also within the scope of the present disclosure. These cores may include airfelt-free cores, SAP/pulp cores, pulp cores, or other cores known to those of skill in the art.

Barrier Leg Cuffs

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present in the crotch region 7. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 or the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

Front and Rear Ears

In a form, the absorbent article may comprise front ears 46 and rear ears 40. The ears may be an integral part of the chassis, such as formed from the topsheet 24 and/or backsheet 25 as side panel. Alternatively, as represented on FIG. 1, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Liquid Management System (LMS)

One function of the LMS 50 is to quickly acquire the fluid and distribute it to the absorbent core 28 in an efficient manner. The LMS 50 may comprise one or more layers, which may form a unitary layer or may remain as discrete layers which may be attached to each other. The LMS 50 may comprise two layers: a distribution layer 54 and an acquisition layer 52 disposed between the absorbent core and the topsheet, but the present disclosure is not limited to such a configuration.

The LMS 50 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

Distribution Layer

The LMS 50 may comprise a distribution layer 54. The distribution layer 54 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

Figure 9:
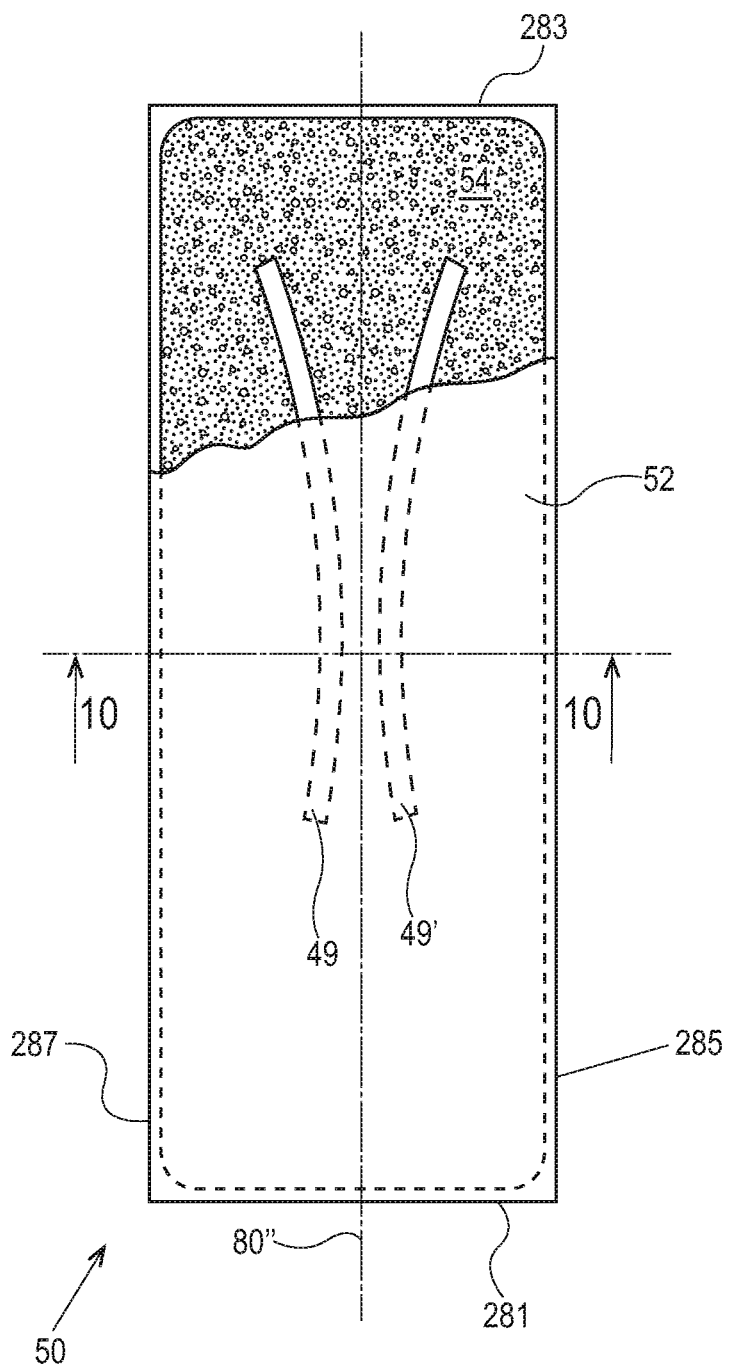
FIG. 9 is a top view of a LMS of the absorbent article of FIG. 4 with some layers partially removed in accordance with the present disclosure.
Figure 10:
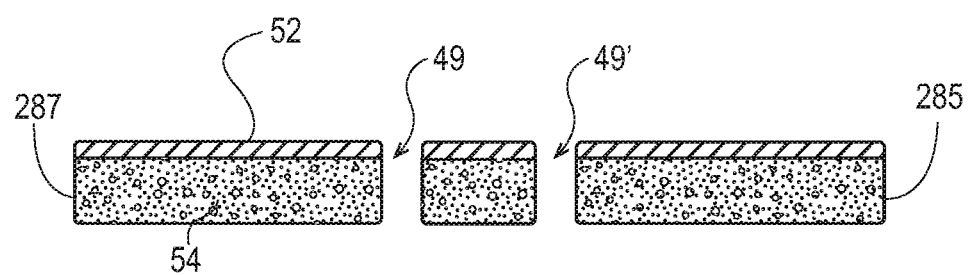
FIG. 10 is a cross-sectional view of the liquid management system taken about line 10-10 of FIG. 9 in accordance with the present disclosure.

The example LMS 50 of the absorbent article of FIGS. 4-5 is shown in isolation in FIGS. 9-10 where FIG. 10 is a cross-sectional view of the LMS 50 taken about line 10-10 of FIG. 9. The LMS 50 may comprises a front side 281, a rear side 283, and two longitudinal sides 285, 287 joining the front side 281 and the rear side 283. The LMS 50 may also comprise a generally planar top side with a surface area and a generally planar bottom side with a surface area. The front side 281 of the LMS is the side of the LMS intended to be placed towards the front waist edge 10 of the absorbent article. The LMS 50 may have a longitudinal axis 80" corresponding substantially to the longitudinal axis 80 of the absorbent article, as seen from the top in a planar view as in FIG. 1. In the illustrated form, the LMS 50 comprises a distribution layer 54 and an acquisition layer 52 which cooperate to define the channels 49, 49'. In other forms, less than all of the layers of the LMS 50 may define the channel such that at least one layer of the LMS 50 is continuous while another layer of the LMS 50 is discontinuous.

Acquisition Layer

The LMS 50 may alternatively or additionally comprise an acquisition layer 52. The acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The acquisition layer 52 may comprise air or wet-laid cellulosic, cross-linked cellulosic, or synthetic fibers, or blends thereof. The acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded.

Channels in Liquid Management System

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, BM or other bodily exudates within the absorbent article, leading to reduced leakage and skin contact. Channels in the LMS 50 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Similar to the channels in the absorbent core 28, a channel in the LMS 50 may be any region in a layer, or extending through more than one layer, that has a substantially lower basis weight or thickness than the surrounding material, as set forth in the definition of "channel" above. The channels in the LMS 50 may also serve to reduce the tension forces to enable controlled bending and maintain the LMS 50 in close proximity to the absorbent core 28. Thus, the presence of channels in the LMS 50, which may or may not be aligned with any channels in an underlying absorbent core 28, may generally function as hinges to allow for a more flexible composite structure. In some cases, for example, the channels of the LMS 50 allow for the LMS 50 to move toward the absorbent core 28 in a controlled bending arrangement, thereby limiting the separation between the LMS 50 and the absorbent core 28. Moreover, a channel in the LMS 50 may assist in the routing of fluid or other bodily exudates from one region of the absorbent article 20 to another region of the absorbent article 20. Such routing may desirably improve the overall distribution of fluid through the absorbent article 20 and may lead to increase in comfort, wearability, or longevity of the article.

For multi-layered LMSs, the channels may be present in one or more layers of the LMS 50 and may vary in their dimensions in all three planes of reference. The width of a given channel in the LMS 50 may vary in the longitudinal direction (i.e., in a direction substantially parallel to the longitudinal axis of the absorbent article). A channel may also have a different width, length, and/or volume in front of a lateral axis or lateral separation element of the absorbent article than behind the lateral axis or lateral separation element. The channels of the LMS 50 may have a range of widths, lengths, shapes, volumes, and patterns, similar to the channels described above with regard to the absorbent core 28.

One or more channels in the LMS 50 may at least partially overlap, or fully overlap, a channel in the absorbent core 28, creating a deeper recess in the overlapping regions. For forms where the LMS 50 includes more than one layer, the layer closest to the absorbent core 28 may include a channel. One or more layers in the structure, such as the topsheet 24, an acquisition layer 52, distribution layer 54, or other layers, may be bonded to an element of the absorbent core 28 in this region to increase the depth of the combined channel. In a form, the channel in the acquisition layer 52 of the LMS 50 and the channel in the absorbent core 28 are coincident such that the channels are completely overlapping. In another form, channels in the LMS and storage layers have no overlapping area. Other forms have a vertical overlap between the channels in the two layers that encompass the intervening range such that they partially overlap.

Referring again to FIGS. 1-5, the LMS 50 in the illustrated example is shown defining two channels 49, 49'. The channels 49, 49' are at least partially oriented in the longitudinal direction of the absorbent article 80 (i.e., has a longitudinal vector component). Other channels in the LMS may be at least partially oriented in the lateral direction (i.e., has a lateral vector component), or in any other direction, and the channels in the LMS 50 may be continuous or intermittent. Some channels in the LMS may be round, oblong, square, rectangular, triangular or any other suitable shape. The channels may be formed in various ways. For example, the channels may be formed by zones within the LMS 50 which may be substantially free of, or free of, acquisition or distribution material.

The channels of the LMS 50 may be present at least at the same longitudinal level as the lateral axis 90 in the absorbent article, as represented in FIG. 1 with the two longitudinally extending channels 49, 49'. The channels may also extend from the crotch region 7 or may be present in the front waist region 5 and/or in the rear waist region 6 of the absorbent article. In FIG. 1, the channels 49, 49' are generally coincident with channels 26, 26', with channels 26, 26' having a longer length in the longitudinal direction towards the front waist edge 10 of the absorbent article 20.

The LMS 50 may define any suitable number of channels, such as at least one or more than two channels. Shorter channels may also be present, for example in the rear waist region 6 or the front waist region 5 of the LMS 50. The channels of the LMS 50 may comprise one or more pairs of channels symmetrically arranged, or otherwise arranged relative to the longitudinal axis 80 and/or the lateral axis 90, or other transverse axis. The channels may extend substantially longitudinally or substantially laterally.

At least some or all of the channels in the LMS 50 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the topsheet 24 to the backsheet 25 together through a channel of the LMS 50. Typically, an adhesive may be used to bond the topsheet 24 and the backsheet 25 through the channels, but it is possible to bond via other known processes, such as pressure bonding, ultrasonic bonding, heat bonding, or combination thereof. The topsheet 24 and the backsheet 25 may be continuously bonded or intermittently bonded along or within portions of or all of the channels.

In a form, referring to FIG. 1, the LMS 50 may comprise at least two channels (e.g., 49, 49'). These channels may be free of, or substantially free of (e.g., less than 10%, less than 5%, less than 3%, less than 2%, or less than 1%), non-woven material or cross-linked cellulose fibers and may be at least partially oriented in the longitudinal direction and/or may be at least partially oriented in the lateral direction.

While portions of the channels 26, 26' of the absorbent core 28 and the channels 49, 49' of the LMS 50 shown in FIGS. 1-10 are generally aligned, this disclosure is not so limited. In fact, as is to be appreciated, particular arrangements of the channels in an LMS 50 and/or an absorbent core 28 may vary.

Pants

An alternate configuration for absorbent articles is one for absorbent pants in which the central chassis structure does not extend to, or form, the front and rear waist edges of the pant. Rather, an elasticized belt structure entirely encircles the wearer's waist and forms the waist edge about the entire pant, and the side/hip panels. The central chassis is joined to the belt structure, usually on the inside thereof, with its ends disposed at locations in the front and rear waist regions somewhat below the waist edges of the belt structure. The elastic belt is usually relatively wide (in the longitudinal direction) and elastically stretchable in the lateral direction. It entirely encircles the wearer's waist, and thereby covers a relatively large amount of the wearer's skin. This configuration is sometimes known as a "belt" or "balloon" configuration (hereinafter, "belt" configuration).

In more detail, an absorbent article may have a front region, a rear region, and a crotch region disposed therebetween, further comprising a liquid permeable topsheet, a backsheet, and an absorbent core disposed between the topsheet and the backsheet. The article then may have a central chassis occupying the crotch region, and a belt structure disposed about the central chassis, the belt structure overlaying the backsheet to the outside thereof in the front and rear regions, and the belt structure overlapping and extending laterally and longitudinally outward from the chassis. The belt structure may comprise an outer nonwoven and an inner nonwoven and have elastic strands therebetween. The belt structure may further have a front belt portion having a front waist edge, and front left and right side edges; and a rear belt portion having a rear waist edge and rear left and right side edges, wherein the respective front and rear left side edges and the respective front and rear right side edges are joined, forming a waist opening and left and right leg openings.

Any pant configuration may have any of the article components described herein, for example, the topsheet, backsheet, core, barrier cuffs, and/or liquid management system layers described herein, along with the odor control composition and its placement. Further descriptions and embodiments of pant configurations may be found in U.S. Ser. No. 62/210635.

Placement of Zeolites

The placement of the zeolites of the present invention may be in one or more of numerous positions. In some embodiments, the zeolites may be deposited directly into the core, for example, inside the core wrap or mixed into the SAP. This particularly secures the zeolites in place, as it is enclosed and secured inside the core wrap. It also ensures that the odor control composition is not visible when the article is viewed from the outside, ie., from either the topsheet side or the backsheet side.

The zeolites may be placed in the absorbent core among the SAP particles. In some embodiments, the zeolites may placed on only one substrate, that is, on only the first absorbent layer or on only the second absorbent layer, or may be placed on both absorbent layers. The zeolites may be placed in a stripe about 20 mm wide in the center of the absorbent core. In some embodiments, at least about 50%, about 60%, about 70%, about 80%, or about 90% of the zeolites are placed within about 10 mm or 15 mm of the lateral center of the absorbent core. In general, the zeolites may be not visible from the outside of the absorbent article.

The zeolites of the present invention may be disposed between the core wrap and the liquid management system. For example, the zeolites may be disposed between the distribution layer and the core wrap. In some cases, the zeolites may be disposed between an acquisition layer and the core wrap, between an acquisition layer and the distribution layer, between two acquisition layers, or between an acquisition layer and the topsheet. One advantage of placement within or between the liquid management system and the core wrap is that such placement may limit interaction with glues and/or core materials and in general, limit the zeolite's interaction with the functions of other components. In many cases, it may be desired that the zeolites be not visible when an open article is viewed from the top (an observer looking at the topsheet side of the article) or when viewed from the backsheet side of the article. The zeolites in general may be disposed such that at least two or three layers of article components are above it towards the topsheet of the article.

In some cases, the zeolites may be placed over at most about 25%, 30%, 35%, 40%, 45%, 50%, 55%, 60%, 65%, 70%, 75%, 80%, 85%, 90%, 95%, or 100% of a surface area. In some cases, the zeolites may be placed on at most about 80% of the core wrap surface area.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A disposable absorbent article having a longitudinal centerline and a lateral centerline, a front waist region with a front waist edge, a rear waist region with a rear waist edge, a crotch region disposed between the front waste region and the rear waist region, and two spaced apart longitudinal side edges joining the front waist edge to the rear waist edge and comprising an assembly of components including a topsheet, a backsheet, and an absorbent core therebetween;
   wherein the absorbent core is substantially free of cellulose fibers; and
   wherein the absorbent core comprises a mixture of at least two types of zeolites,
   wherein the first type of zeolite is characterized by:
   a) a FAU (Faujasite) framework wherein:
      i) the sodium content expressed as $Na_2O$ is below 10 wt %; and
   wherein the second type of zeolite is characterized by:
   b) a MFI (Mordenite Framework Inverted) framework wherein:
      i) the sodium content expressed as $Na_2O$ is below 1 wt %; and
   wherein the third type of zeolite is characterized by:
   c) a MOR (Mordenite) framework wherein:
      i) the sodium content expressed as $Na_2O$ is below 5 wt %.

2. The disposable absorbent article of claim 1, wherein the zeolites are selected from the group consisting of:
   a) a FAU framework wherein:
      i) the sodium content expressed as $Na_2O$ is below 2 wt %;
      ii) the silica to alumina ratio is greater than 4.0;
   b) a MFI framework wherein:
      i) the sodium content expressed as $Na_2O$ is below 0.1 wt %;
      ii) the silica to alumina ratio is less than 500; and
   c) a MOR framework wherein:
      i) the sodium content expressed as $Na_2O$ is below 1 wt %.

3. The disposable absorbent article of claim 1, wherein the zeolites are selected from the group consisting of:
   a) a FAU framework wherein:
      i) the sodium content expressed as $Na_2O$ is below 2 wt %;
      ii) the silica to alumina ratio is greater than 5.0;
      iii) the silica to alumina ratio is less than 100.0;
   b) a MFI framework wherein:
      i) the sodium content expressed as $Na_2O$ is below 0.1 wt %;
      ii) the silica to alumina ratio is less than 500;
      iii) the silica to alumina ratio is greater than 25; and
   c) a MOR framework wherein:
      i) the sodium content expressed as $Na_2O$ is below 1 wt %;
      ii) the silica to alumina ratio is less than 50;
      iii) the silica to alumina ratio is greater than 10.

4. The disposable absorbent article of claim 1, wherein the zeolites are mixed with at least one additional component selected from the group consisting of silica, alumina, clay, silica-aluminate, and a metal oxide.

5. The disposable absorbent article of claim 4, wherein the ratio of the silica to the zeolites is from about 1:1 to about 3:1.

6. The disposable absorbent article of claim 1, wherein the zeolites comprise from about 10% to about 90% of an FAU framework; and the zeolites comprise from about 10% to about 90% of an MFI framework.

7. The disposable absorbent article of claim 1, wherein the zeolites comprise from about 10% to about 90% of an MOR framework; and the zeolites comprise from about 10% to about 90% of an MFI framework.

8. The disposable absorbent article of claim 1, wherein the zeolites comprise from about 10% to about 90% of an FAU framework; the zeolites comprise from about 10% to about 90% of an MFI framework; and the zeolites comprise from about 0% to about 90% of an MOR framework.

9. The disposable absorbent article of claim 1, wherein the zeolites comprise from about 25% to about 75% of an FAU framework; and the zeolites comprise from about 25% to about 75% of an MFI framework.

10. The disposable absorbent article of claim 1, wherein the zeolites comprise from about 20% to about 70% of an FAU framework; the zeolites comprise from about 20% to about 70% of an MFI framework; and the zeolites comprise from about 0% to about 10% of an MOR framework.

11. The disposable absorbent article of claim 1, wherein the absorbent core comprises less than about 20% by weight of cellulose fibers.

12. The disposable absorbent article of claim 1, wherein the absorbent core comprises less than about 2% by weight of cellulose fibers.

13. The disposable absorbent article of claim 1, wherein the absorbent core is free of cellulose fibers.

14. The disposable absorbent article of claim 1, wherein the absorbent core comprises a center, and wherein at least 70% of the zeolites are placed in a stripe about 20 mm wide in the center of the absorbent core.

15. The disposable absorbent article of claim 1, wherein the absorbent core further comprises silica.

16. The disposable absorbent article of claim 1, wherein the zeolites comprise frameworks selected from the group consisting of:
   a) an FAU framework, wherein:
      i) the sodium content expressed as $Na_2O$ is below 10 wt %;
      ii) the silica to alumina ratio is greater than 4.0;
   b) an MFI framework, wherein:
      i) the sodium content expressed as $Na_2O$ is below 1 wt %;
      ii) the silica to alumina ratio is less than 500; and
   c) an MOR framework, wherein:
      i) the sodium content expressed as $Na_2O$ is below 5 wt %.

17. The disposable absorbent article of claim 1, wherein the disposable absorbent article further comprises at least one additional component selected from the group consisting of:
   a) a liquid management system comprising an acquisition layer and a distribution layer, the liquid management system disposed between the topsheet and the absorbent core;

b) a fastening system for joining the front waist region to the rear waist region when the absorbent article is worn;
c) barrier cuffs lying adjacent and inboard one of the longitudinal side edges;
d) gasketing cuffs lying between the longitudinal side edge and the barrier cuff;
e) front ears disposed in the front waist region;
f) back ears disposed in the rear waist region; and
g) at least one hot melt adhesive composition suitable for joining at least two absorbent article components together.

18. A disposable absorbent article of claim 1 having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge and comprising an assembly of components including:
a) a topsheet;
b) a backsheet underlying the topsheet;
c) an absorbent core comprising two substrates;
wherein each substrate has a layer of absorbent material disposed thereon;
wherein each substrate has a layer of fibrous thermoplastic material at least partially in contact with the layer of absorbent material; and
wherein the absorbent core comprises the mixture of at least two zeolites with the absorbent material.

19. A disposable absorbent article according to claim 1 having a longitudinal centerline and a lateral centerline, a front waist region with a front waist edge, a rear waist region with a rear waist edge, a crotch region disposed between the front waist region and the rear waist region, and two spaced apart longitudinal side edges joining the front waist edge to the rear waist edge and comprising an assembly of components including:
a) a topsheet;
b) a backsheet underlying the topsheet;
c) an absorbent core disposed between the topsheet and the backsheet, the absorbent core being free of cellulose and comprising a mixture of three zeolites;
wherein the zeolites comprise frameworks selected from the group consisting of:
a) an FAU framework wherein:
   i) the sodium content expressed as $Na_2O$ is below 2 wt %;
   ii) the silica to alumina ratio is greater than 5.0; and
   iii) the silica to alumina ratio is less than 100.0;
b) an MFI framework wherein:
   i) the sodium content expressed as $Na_2O$ is below 0.1 wt %;
   ii) the silica to alumina ratio is less than 500; and
   iii) the silica to alumina ratio is greater than 25; and
c) an MOR framework wherein:
   i) the sodium content expressed as $Na_2O$ is below 1 wt %;
   ii) the silica to alumina ratio is less than 50; and
   iii) the silica to alumina ratio is greater than 10.

* * * * *